United States Patent

Chan et al.

[11] Patent Number: 6,096,246
[45] Date of Patent: Aug. 1, 2000

[54] PHOTOCHROMIC NAPHTHOPYRANS, COMPOSITIONS AND ARTICLES CONTAINING THEM

[75] Inventors: You-Ping Chan, Lyons; Nathan Bryson, Millery, both of France

[73] Assignee: Corning Incorporated, Corning, N.Y.

[21] Appl. No.: 09/171,707

[22] PCT Filed: Jul. 16, 1997

[86] PCT No.: PCT/US97/13723

§ 371 Date: Oct. 23, 1998

§ 102(e) Date: Oct. 23, 1998

[87] PCT Pub. No.: WO98/04937

PCT Pub. Date: Feb. 5, 1998

Related U.S. Application Data

[60] Provisional application No. 60/029,105, Oct. 21, 1996.

[30] Foreign Application Priority Data

Jul. 25, 1996 [FR] France .................................. 96 09384

[51] Int. Cl.⁷ ........................... C08K 5/15; C07D 311/92
[52] U.S. Cl. ................. 252/586; 524/110; 526/268; 549/331; 549/389; 549/58; 549/60; 546/282.7; 548/440
[58] Field of Search ............................ 252/586; 549/389, 549/331

[56] References Cited

U.S. PATENT DOCUMENTS

| | | | |
|---|---|---|---|
| 3,627,690 | 12/1971 | Casella et al. ............................ | 549/389 |
| 4,826,977 | 5/1989 | Heller et al. ............................... | 544/70 |
| 4,931,221 | 6/1990 | Heller ....................................... | 252/586 |
| 5,200,116 | 4/1993 | Heller ....................................... | 252/586 |
| 5,458,814 | 10/1995 | Kumar et al. ............................. | 252/586 |
| 5,573,712 | 11/1996 | Kumar et al. ............................. | 252/586 |
| 5,656,206 | 8/1997 | Knowles et al. .......................... | 252/586 |

FOREIGN PATENT DOCUMENTS

| | | |
|---|---|---|
| 0 246 114 | 11/1987 | European Pat. Off. . |
| 0 401 958 | 12/1990 | European Pat. Off. . |
| 92/01959 | 2/1992 | WIPO . |

*Primary Examiner*—Bernard Dentz
*Attorney, Agent, or Firm*—Angela N. Nwaneri; Peter Rogalskyj

[57] ABSTRACT

The invention relates to photochromic compounds of general formula (I), in which: $R_3$ and $R_5$ are $C_1$–$C_6$ alkoxy groups and the rest of the R groups represent various substituents.

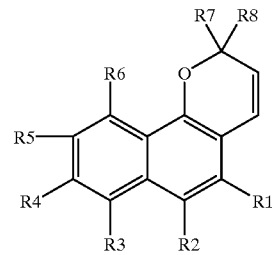

(I)

21 Claims, No Drawings

PHOTOCHROMIC NAPHTHOPYRANS, COMPOSITIONS AND ARTICLES CONTAINING THEM

This application is a 371 of PCT/US97/13723 filed Jul. 16, 1997 and also claims domestic priority from Verified Provisional Application Ser. No. 60/029,105 filed Oct. 21, 1996.

The present invention concerns novel compounds of the naphthopyran type, presenting, in particular, photochromic properties. It also concerns the photochromic compositions and ophthalmic articles (for examples, lenses) which contain naphthopyrans.

Photochromic compounds are capable of changing colors due to the influence of poly- or monochromatic light (for example, UV radiation) and to recover their initial color again when the luminous irradiation stops, or under the influence of poly- or monochromatic light different from the first one, or under the influence of temperature and/or poly- or monochromatic light different from the first one.

These photochromic compounds find applications in different fields, for example, in the manufacture of ophthalmic lenses, contact lenses, sun protection glasses, filters, optical systems of cameras or photographic apparatuses or other optical and observation devices, paneling, decorative objects, display elements or for the storage of information by optical inscription (coding).

In the field of ophthalmic optics, and in particular in eyeglass wear, a photochromic lens, comprising one or more photochromic compounds, must present:

high transmission in darkness or in the absence of sunlight, low transmission (high colorability) under similar irradiation, an adapted coloration or discoloration kinetics, a tint that is acceptable to the consumer (preferably gray or chestnut brown) with, preferably, maintenance of the selected tint during the coloration or discoloration of the lens, maintenance of the performances of the properties in a temperature range of 0–40° C., high durability. because the targeted objectives are sophisticated and hence corrective lenses are expensive.

These lens characteristics are in fact determined by the active photochromic compounds which must in addition be compatible with the organic material or mineral constituting the lens.

It should also be noted that the obtention of a gray or chestnut brown tint should require the use of at least two photochromes of different colors, that is, having different maximum absorption wavelengths in the visible range. This association also places other requirements on photochromic compounds. In particular the coloration and discoloration kinetics of the two or more associated active photochromic compounds must be essentially identical. The same applies to their stability over time and also, to their compatibility with a plastic or mineral support.

Among the numerous photochromic compounds described in the prior art, one can cite the naphthopyrans described in U.S. Pat. Nos. 3,567,605, 3,627,690, 4,826,977, 5,200,116, 5,458,814 and Research Disclosure No. 36144:

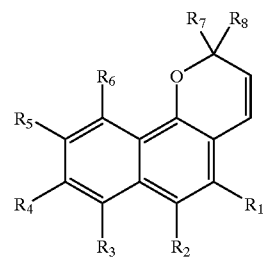

The claim is made that these compounds satisfy the above defined specifications. In fact, whereas these compounds have in fact one or more of the desired basic properties, such as high transmission in darkness and high colorability under solar irradiation, all the compounds described to this day do not have the complete combination of desired properties required for the production of satisfactory articles that can be manufactured industrially Although the prior art teaches how to modify the discoloration kinetics by the presence of a methyl group in R1 and R2, it does not teach how to modify the profile of the visible spectrum of the activated form (exposure to UV). The compounds of the prior art are generally orange or red with a principal absorption band in the visible range.

It is the merit of the applicant to have found, surprisingly, that the presence of at least two alkoxy groups, at R3 and R5, allowed the obtention of photochromes having two intense absorption bands in the visible range and at high values of $\lambda_{max}$. The compounds of the invention thus cover a part of the visible spectrum (400–700 nm).

Thus, the present invention concerns compounds, particularly photochromic compounds, having the following general formula (I):

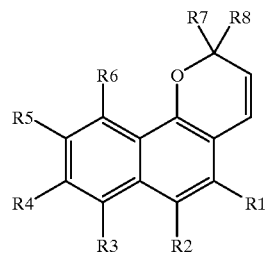

in which:

R1, R2, R4 and R6 are identical or different and they represent, independently hydrogen, a halogen, preferably fluorine, chlorine or bromine, a linear or branched alkyl group comprising 1–12 carbon atoms, a cycloalkyl or bicycloalkyl group comprising 3 to 12 carbon atoms, a linear or branched alkoxy group comprising 1–12 carbon atoms, a linear or branched haloalkyl or haloalkoxy group comprising 1–6 carbon atoms, preferably a fluoroalkyl group, a linear or branched alkenyl or alkynyl group comprising 1–12 carbon atoms, preferably a vinyl or allyl group, a methacryloyl group or an acryloyl group, an epoxy group having the formula//insert a, p.4// in which n=1, 2 or 3 an aryl or aryloxyl group, whose aryl group comprises 6–24 carbon atoms, or a heteroaryl or heteroaryloxy group whose heteroaryl group comprises 4–24 carbon atoms and at least one heteroatom selected from the group consisting of sulfur, oxygen and nitrogen, the aryl or heteroaryl group optionally substituted by at least one substituent selected from:

a halogen, preferably fluorine, chlorine or bromine, a linear or branched alkyl group comprising 1–6 carbon atoms, a linear or branched alkoxy group comprising 1–6 carbon atoms, a linear or branched haloalkyl or haloalkoxy group comprising 1–6 carbon atoms, preferably a fluoroalkyl group, an —$NH_2$ group, an NHR group, where R represents a linear or branched alkyl group comprising 1–6 carbon atoms, a NR'R" group, where R' and R", which may be identical or different, independently represent a linear or branched alkyl group comprising 1–6 carbon atoms or they represent, together with the nitrogen atom to which they are bound, a 5–7-member ring which can comprise at least one other heteroatom selected from the group of oxygen, sulfur and nitrogen, said nitrogen being optionally substituted by a linear or branched alkyl group comprising 1–6 carbon atoms, an aralkyl or heteroalkyl group whose linear or branched alkyl group comprises 1–4 carbon atoms and whose aryl and heteroaryl groups are as defined above, an —$NH_2$, —NHR, NR'R", $CONH_2$, CONHR or CONR'R" group, where R, R' and R" are as defined above, an OCOR' or COOR' group, where R' represents a linear or branched alkyl group comprising 1–6 carbon atoms or a cycloalkyl or bicycloalkyl group comprising 3–12 carbon atoms or an aryl or heteroaryl group as defined above, a polyether, polyamide, polycarbonate, polycarbamate, polyurea or polyester residue;

R7 and R8 are identical or different and they represent independently:

a linear or branched alkyl group comprising 1–12 carbon atoms, a cycloalkyl group comprising 3–12 carbon atoms, an aryl or heteroaryl group as defined above for R1, R2, R4 and R6, the julolidin-9-yl group, or the two groups R7 and R8 together form an adamantyl, norbornyl, fluorenylidene or di(C1–C6 alkyl) anthracenylidene or spiro (C5–C6 cycloalkyl) anthracenylidene group; characterized in that R3 and R5 are identical or different and they each represent a linear or branched alkoxy group comprising 1–6 carbon atoms.

Among the substituents that can be considered for the compounds of formula (1) according to the invention, groups should be considered that comprise and/or form at least one function which can be polymerized and/or crosslinked, which group are preferably selected from the following list: alkenyl, advantageously vinyl, methacryloyl, acryloyl, acryloxyalkyl, methacryloxyalkyl or epoxy.

Thus, the photochromic compounds according to the invention can be monomers, of different types or not, that can react with each other or with other comonomers to form homopolymers and/or copolymers that bear a photochromic functionality and possess mechanical properties of macromolecules. It follows that one of the objects of the present invention consists of these homopolymers or copolymers comprising (co)monomers and/or of crosslinked compounds, that, at least in part, consist of photochromic compounds (I) according to the invention.

In the same order of ideas, the above-mentioned compounds (I) can be crosslinking agents that have reactive functions capable of allowing the formation of bridges between chains of polymers of photochromic nature or not. The crosslinked compounds that can be obtained in this manner also are a part of the present invention.

In a generally preferred manner, the alkoxy groups are methoxy groups. Preferred compounds of the invention have the following formulas (I1 and I2):

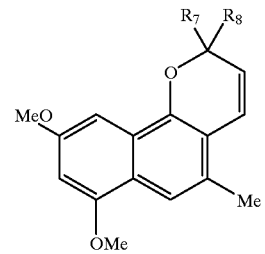

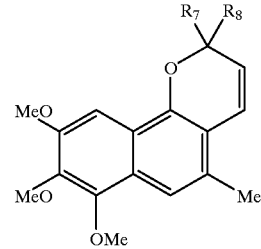

where R7 and R8 are polyaromatic or polyheteroaromatic groups that are optionally substituted by one or more C1–C5 alkoxy groups, C1–C6 amine or alkyl groups or C6–C12 aryl groups.

It is the merit of the applicant to have disclosed these compounds, because they present particularly advantageous photochromic properties. More precisely, they have a strong colorability with two absorption bands in the visible range with high $\lambda_{max}$ values.

These compounds are also preferably stable and compatible with matrices made of organic polymer or mineral material, both in the form included in the matrix and in the form of the coating.

In a solution or in the polymer matrix, the compounds according to the invention are colorless or slightly colored in the initial state and they rapidly develop an intense coloration under UV light (365 nm) or a luminous source of the solar type. They rapidly recover their initial color when the irradiation stops.

The compounds of the invention can be obtained by the condensation of a derivative of 1-naphthol that is suitably substituted and either a derivative of propargyl alcohol (the condensation, according to this variant, can be carried out in solvents such as toluene, xylene or tetrahydrofuran and, optionally, in the presence of a catalyst such as p-toluenesulfonic acid, chloroacetic acid or acid aluminic acid)

or a derivative of acrolein (in the presence of titanium tetraethylate).

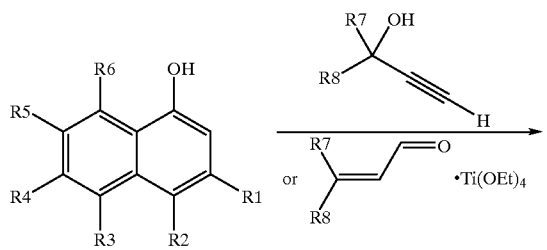

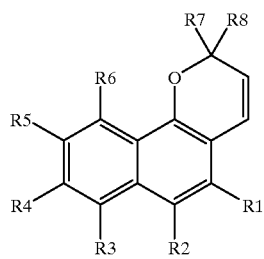

These synthetic pathways are classical and have been described in the above-mentioned references of the prior art as well as in European Patent No. A-0,562,915. The ketones (R7)(R8)CO are either commercially available or easily synthesized by the classical methods, for example, the Friedel-Krafts reaction from an acid chloride. The derivatives of propargyl alcohol are then obtained by the reaction of lithium acetylide with the corresponding ketones. The derivatives of acrolein can be obtained by rearrangement of the corresponding derivative of propargyl alcohol in an acidic medium (see J. Org. Chem. 1977, Vol. 42, p. 3403, Edens et al.).

The derivatives of 1-naphthol are obtained by various methods adapted from the literature. Below we give some references on methods that allow the synthesis of the compounds of the invention.

Method 1: Sibi et al., Org. Chem. 1986, Vol. 51, pp. 271–273.

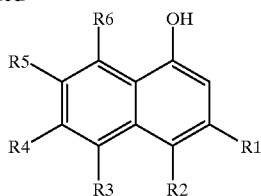

Key: 1 MeLi or LDA or s-BuLi
Method 2: U.S. Pat. No. 5,200,116 (Example 2):

Method 3: Johnson et al. Org. React. 1951, Vol. 6, p. 1.

Regarding the application of the compounds according to the present invention, it should be noted that they can be used as a photochromic material dispersed in the composition of a polymer matrix. They can also be used in solution.

A photochromic solution can be obtained by dissolving the compound in an organic solvent, such as toluene, dichloromethane, tetrahydrofuran or ethanol. The solutions obtained are generally colorless and transparent. When exposed to sunlight, they develop a strong coloration and they recover the color of this state when placed in a zone with lesser exposure to solar radiation or, in other words, when they are no longer exposed to UV radiation. In general a very low concentration of products (on the order of 0.01–5%) is sufficient to obtain an intense coloration.

The most interesting applications are those in which the photochrome is dispersed uniformly within or on the surface of a polymer, copolymer or mixture of polymers. The implementation methods that can be considered are of a great variety. Among those known to a person skilled in the art, one can cite, for example, diffusion in the (co)polymer, from a suspension or solution of the photochrome, in a silicone oil, in an aliphatic or aromatic hydrocarbon, in a glycol, or from another polymer matrix. Currently the diffusion is carried out at a temperature of 50–200° C. for a duration of 15 min to several hours, depending on the nature of the polymer matrix. Another implementation technique consists in mixing the photochrome in a formulation of polymerizable materials, in depositing this mixture on a surface or in a mold and in then carrying out the polymerization. These implementation techniques and others are described in the article by CRANO et al. "Spiroxazines and their use in photochromic lenses," published in Applied Photochromic Polymer Systems. Publishers Blackie and Son Ltd., 1992. According to a variant of the invention, it is also possible to consider grafting the photochromes onto (co) polymers. Thus, another object of the invention consists of the (co)polymers grafted with at least one of the photochromes described above.

As examples of preferred polymer materials for optical applications of the photochromic compound according to the invention, one can mention the following products:

alkyl, cycloalkyl, aryl or arylalkyl poly(mono-, di-, tri-, tetra)acrylate or poly(mono-, di-, tri-, tetra) methacrylate, optionally halogenated or comprising at least ether and/or ester and/or carbonate and/or carbamate and/or thiocarbamate and/or urea and/or amide group; polystyrene, polycarbonate (e.g., bisphenol A polycarbonate, poly(carbonate of diallyl diethylene glycol), polyepoxy, polyurethane, polythiourethane, polysiloxane, polyacrylonitrile, polyamide, aliphatic or aromatic polyester, vinyl polymers, cellulose acetate, cellulose triacetate, cellulose acetate-propionate or polyvinylbutyral, copolymers of two or more types of monomers or mixtures of the above-mentioned polymers, preferably polycarbonate-polyurethane, poly (meth)acrylate-polyurethane, polystyrene-poly(meth) acrylate or polystyrene-polyacrylonitrile, advantageously a mixture of polyester and/or polycarbonate or poly(meth)acrylate.

The quantity of photochrome used depends on the desired degree of darkening. In particular, it is used in a quantity of 0.001–20 wt %. The photochromic compounds according to the invention can be used alone or in a mixture with other products to form a composition that can be in solid or liquid form, for example, in a solution or in a dispersion, as has already been mentioned above. These compositions, which constitute another object of the invention, can comprise one or more compounds (I) according to the invention and other complementary photochromic compounds which allow the obtention of dark colorations, for example, gray or brown, which the public desires in applications such as ophthalmic or sun-protection eyewear. These additional photochromic compounds can be those known to a person skilled in the art and described in the literature, for example, chromenes (U.S. Pat. Nos. 3,567,605, 5,238,981, World Patent No. 9,422,850, European Patent No. 562,915), spiropyrans or naphthospiropyrans (U.S. Pat. No. 5,238,981) and spiroxazines (CRANO et al., "Applied Photochromic Polyrmer Systems," Publishers Blackie & Son Ltd., 1992, Chapter 2).

These compositions according to the invention can also comprise:
nonphotochromic dyes allowing the adjustment of the tint,
and/or one or more stabilizers, such as, for example, an antioxidant,
and/or one or more anti-UV screens,
and/or one or more anti [free] radical agents,
and/or deactivators that deactivate the states of photochemical excitation.

These additives can allow the improvement of the durability of said compositions.

According to another one of its aspects pertaining to the application of the photochromic compounds (I), the present invention also relates to ophthalmic articles, such as articles of ophthalmic or sun protection eyewear articles, comprising at least one compound according to the invention and/or at least one (co)polymer formed, at least in part, of repeating units derived from compounds having formula (I), and/or at least one composition comprising compounds (I), according to the invention, as defined above, and/or at least one matrix, as defined above, made of an organic polymer material or a mineral material or a mineral-organic hybrid material incorporating at least one compound of the invention.

In practice, the articles to which the present invention applies more particularly are photochromic ophthalmic or sun-protection lenses, glass paneling (glasses for buildings, for locomotion devices, automobiles), optical devices, decorative articles, sun-protection articles, information storage, etc.

The present invention will be better understood in the light of the following examples of synthesis and photochromic validation of compounds having the general formula (I).

EXAMPLES

Synthesis and properties of photochromic compounds 1–9 according to the invention Example 1

Synthesis of compound (1); 2,2-bis(4-methoxyphenyl)-5-methyl-7,9-dimethoxy-[2H]-naphtho[1,2-b]pyran Step 1: 5,7-Dimethoxy-3-methyl-1-naphthol is synthesized from N,N-diethyl-3,5-dimethoxybenzamide and 3-bromo-2-methylpropene according to the method described by Sibi et al. (J. Org. Chem. 1986, Vol. 51, pp. 271–273). The yield is approximately 50%.

Step 2: 1,1-bis(p-dimethoxyphenyl)-2-propyn-1-ol is obtained by reacting lithium acetylide (diamine complex) with 4,4'-dimethoxybenzophenone in DMSO followed by hydrolysis and extraction with toluene. The yield is quantitative.

Step 3: The compound obtained in step 1 (2 g) is reacted with that obtained in step 2 (2.23 g) in 30 mL of toluene in the presence of a catalytic quantity of p-toluenesulfonic acid at 25° C. for 2 h. The medium is then washed with water containing 10% sodium bicarbonate, evaporated to dryness, and then the photochrome is separated by chromatography on a silica column using as eluant a heptane/diisopropyl ether mixture (70/30). In this manner 100 mg of compound (I) are obtained in the form of a white powder. The $^1$H NMR confirms the structure of the product.

Example 2

Synthesis of compound (2); 2-(4-methoxyphenyl)-2-(3,4-dimethoxyphenyl)-5-methyl-7,9-dimethoxy-[2H]-naphtho[1,2-b]pyran Step 1: 36.2 g of p-methoxybenzoyl chloride are reacted with the Eq of 1,2-dimethoxybenzene in the presence of 1.1 Eq of aluminum chloride (added in aliquots) at 0° C. in 300 mL of dichloromethane for 1 h. The mixture is then poured into a mixture of 1 kg of ice and 800 mL of concentrated HCl. The organic phase is decanted, and reduced to dryness. In this manner, 53 g of 3,4,4'-trimethoxybenzophenone are recovered.

Step 2: 1-(3,4-Dimethoxyphenyl)-1-(4-methoxyphenyl-2-propyn-1-ol is prepared by reacting 10 g of the ketone of the preceding step with 1.5 Eq of lithium acetylide at 20° C. for 3 h. The medium is then hydrolyzed in a water/ice mixture and the product is extracted with toluene and then dried over magnesium sulfate. After filtration and evaporation of the solvent, 10.4 g of the desired product are recovered.

Step 3: The compound (2) is then obtained in a manner similar to that used for compound (1) from 5,7-dimethoxy-3-methyl-1-naphthol and the compound of the preceding step. The structure of the compound is confirmed by NMR spectroscopy.

Example 3

Synthesis of compound (3); 2-(4-methoxyphenyl)-2-(6-methoxy-2-naphthyl)-5-methyl-7,9-dimethoxy-[2H]-naphtho[1,2-b]pyran Step 1: 36 g of p-methoxybenzoyl chloride are reacted with 1 Eq of 6-methoxy-2-bromonaphthalene magnesium in a solution in THF (solution prepared by reacting the bromide with 1.5 Eq of magnesium, followed by filtration) at 0° C. for 2 h. The medium is then poured into a mixture of 300 g of ice and 50 mL of concentrated HCl. The precipitate formed is recovered and washed with water (3×500 mL). After drying, 61 g of 2-(6-methoxynaphth-2-yl)-(4-methoxyphenyl) ketone are obtained.

Step 2: The derivative 2-propyne-1-ol is prepared by reacting 5 g of the ketone from the preceding step with 1.5 Eq of lithium acetylide at 20° C. in 30 mL of DMSO for 3 h. The mixture is then hydrolyzed in a water/ice mixture and the product is extracted with toluene and then dried over magnesium sulfate. After filtration and evaporation of the solvent, 3.7 g of the desired product are recovered.

Step 3: The compound (3) is then obtained in a manner similar to that used for the compound (1) from 5,7-dimethoxy-3-methyl-1-naphthol and the compound of the preceding step. The structure of the compound is confirmed by NMR spectroscopy.

Example 4

Synthesis of compound (4), 2-(4-morpholinophenyl)-2-phenyl-5-methyl-7,9-dimethoxy-[2H]-naphtho[1,2-b]pyran Step 1: 17.3 g of benzoyl chloride and 20 g of phenyl morpholine are mixed in 200 mL of dichloromethane and the medium is cooled at 0° C. 18 g of aluminum chloride are added to it in portions over a period of approximately 30 min. After 1 h of stirring, the medium is poured into a mixture of 300 g of ice and 50 mL of concentrated HCl. The medium is then neutralized with 20% soda and the product is extracted with dichloromethane (2×200 mL). The solution is then reduced to dryness, and then the product is crystallized in diisopropyl ether. 9 g of 4-morpholinobenzophenone are recovered.

Step 2: The derivative 2-propyn-1-ol is prepared by reacting 9 g of 4-morpholinobenzophenone with 1.5 Eq of lithium acetylide at 20° C. in 50 mL of DMSO for 2 h. The medium is then hydrolyzed in a water/ice mixture and the product is extracted with dichloromethane, and then dried over magnesium sulfate. After filtration and evaporation of the solvent, the desired product is recovered with a quantitative yield.

Step 3: 8.7 g of 5,7-dimethoxy-3-methyl-1-naphthol are reacted with 11.5 g of the compound of the preceding step in 100 mL of xylene with reflux for 6 h. The compound (4) is then purified by chromatography on a silica column using as eluant a heptane/ethyl acetate mixture (80/20). The structure of the compound is confirmed by NMR spectroscopy.

Example 5

Synthesis of compound (5); 2-(4-N,N-dimethylaminophenyl)-2-phenyl-5-methyl-7,9-dimethoxy-[2H]-naphtho[1,2-b]pyran Step 1: The derivative 2-propyne-1-ol is prepared by reacting 30 g of 4-(N,N-dimethylamino)benzophenone with 1.5 Eq of lithium acetylide as in step 2 of the preceding example.

Step 2: 4 g of 5,7-dimethoxy-3-methyl-1-naphthol and 5.85 g of the compound of the preceding step are reacted in 50 mL of toluene, with reflux for 3 h in the presence of a catalytic quantity of chloroacetic acid. The medium is then washed with 40 mL of IN soda. The compound is then purified by chromatography on an alumina column using as eluant diisopropyl ether. After evaporation of the solvent, the solid is triturated in 100 mL of heptane. 1.6 g of compound (5) are recovered by filtration. The structure of the compound is by NMR spectroscopy.

Example 6

Synthesis of compound (6); 2-(4-N,N-dimethyaminophenyl)-2-(4-methoxyphenyl)-5-methyl-7,9-dimethoxy-[2H]-naphtho[1,2-b]pyran Step 1: 28 g of p-anisoyl chloride and 20 of N,N-dimethylaniline are mixed in 150 mL of dichloromethane and the medium is cooled at 0° C. 24.2 of aluminum chloride is added to the medium in portions over a period of approximately 30 min. After an additional 30 min of stirring at 20° C., the medium is poured into a mixture of 1 kg of ice and 800 mL of concentrated HCl. Ex tract ion i s carried out with dichloromethane and the medium is then neutralized with 30% soda. After decanting, the organic phase is reduced to dryness, and then dissolved in 100 mL of diisopropyl ether with reflux for 30 min. After one night at ambient temperature, the solution is filtered and 8.6 g of 4-(N,N-dimethylamino)-4'-methoxybenzophenone are recovered.

Step 2: The derivative 2-propyn-1-ol is prepared in a manner similar to the one used for the preceding compound. The desired product is obtained in a quantitative yield.

Step 3: The product of the preceding step is transformed into 4-methoxy-β-(N,N-dimethylaniline)cinnamaldehyde by heating at 50° C. for 3 h in a mixture of 70 mL of acetic acid and 5 mL of water. The isolation of the product is carried out as follows; evaporation of the acetic acid under a vacuum, dissolution in toluene, washing in a 10% sodium bicarbonate solution, followed by evaporation to dryness. In this manner, 9 g of the desired product are obtained.

Step 4: 3 g of 5,7-dimethoxy-3-methyl-1-naphthol are reacted with 3.76 g of Ti(OEt)$_4$ in 50 mL of toluene with reflux for 30 min, and then 3.86 g of the compound of the preceding steps, dissolved in 50 mL of toluene, are added. The mixture is maintained with reflux for 2 h. The medium is then hydrolyzed with 40 mL of water and the organic phase is recovered. Compound (6) is then purified by chromatography on an alumina column using as eluant a mixture of diisopropyl ether/ethyl acetate (90/10) followed by a crystallization in ethanol. In this manner, 2.6 g of a cream-colored powder are obtained. The structure of the compound is confirmed by NMR spectroscopy.

Example 7

Synthesis of compound (7); 2,2-bis(4-N,N-dimethylaminophenyl)-5-methyl-7,9-dimethoxy-[2H]-naphtho [1,2-b]pyran Step 1: The derivative 2-propyn-1-ol is prepared in a manner similar to the one used from the preceding compound from 4,4'-bisdimethylaminobenzophenone and lithium acetylide. The desired product is recovered in a quantitative yield.

Step 2: 2 g of 5,7-dimethoxy-3-methyl-1-naphthol are reacted with 2.7 g of the compound of the preceding step in 50 mL of toluene with reflux for 3 h in the presence of a catalytic quantity of chloroacetic acid. The medium is then washed with 40 mL of 1N soda. The compound is then purified by chromatography on an alumina column using diisopropyl ether as an eluant. After evaporation of the solvent, the solid is triturated in 100 mL of heptane. In this manner, 0.3 g of compound (7) are recovered b y filtration. The structure of the compound is confirmed by NMR spectroscopy.

Example 8

Synthesis of compound (8); 2-(4-N,N-diethylaminophenyl)-2-(4-methylphenyl)-5-methyl-7,9-dimethoxy-[2H]-naphtho[ 1,2-b]pyran Step 1: 22.8 g of p-toluoyl chloride and 20 g of N,N-diethylaniline are mixed in 150 mL of dichloromethane and the medium is cooled to 0° C. 19.7-g of aluminum chloride are added in portions to the medium over a period of approximately 30 min. After 1 additional h of stirring at 20° C., the medium is poured into a mixture of 400 g of ice and 100 mL of concentrated HCl. The extraction is carried out with dichloromethane, followed by neutralization of the medium with 1N soda. After decanting, the organic phase is reduced to dryness and then redissolved in 200 mL of heptane with reflux. After 1 h at ambient temperature, the solution is filtered, and 10.5 g of 4-(N,N-diethylamino)4'-methoxybenzophenone are recovered.

Step 2: The derivative 2-propyne-1-ol is prepared in a manner similar to the one used for the preceding compound, and the desired product is recovered with a quantitative yield.

Step 3: The product of the preceding step is transformed into 4-(N,N-diethylamino)-β(4-methoxyphenyl) cinnamaldehyde by heating at 50° C. for 1 h in a mixture of acetic acid/water as in step 3 of the synthesis of compound (6).

Step 4: 1.48 g of 5,7-dimethoxy-3-methyl-1-naphthol are reacted with 1.9 g of Ti(OEt)$_4$ in 50 mL of toluene with reflux for 30 min, and then 2 g of the compound of the preceding step, which has first been dissolved in 25 mL of toluene, are added. The mixture is maintained with reflux for 1 h with azeotropic distillation of water through a Dean Stark condenser. The medium is then hydrolyzed with 40 mL of water, and the organic phase is recovered. Compound (8) is then purified by chromatography on an alumina column using as eluant, diisopropyl ether followed by the crystallization in ethanol. In this manner, 0.8 g of powder is obtained. The structure of the compound is then confirmed by NMR spectroscopy.

Example 9

Synthesis of compound (9); 2-(julolidin-9-yl)-2-phenyl-5-methyl-7,9-dimethoxy-[2H]-naphtho[1,2-b]pyran Step 1: 8.11 g of benzoyl chloride and 10 g of julolidine are mixed in 100 mL of dichloromethane and the medium is cooled to 0° C. 8.5-g of aluminum chloride are added in portions added to the medium over a period of approximately 30 min. After an additional 2 h of stirring at 20° C., the medium is poured into a mixture of 400 g of ice and 100 mL of concentrated HCl. Extraction is carried out with dichloromethane and the medium is then neutralized with 1N soda. After decanting, the organic phase is reduced to dryness, and then redissolved in 200 mL of heptane with reflux. After 1 h at ambient temperature, the solution is filtered, and 5.5 g of phenyl julolidinyl ketone are recovered.

Step 2: The derivative 2-propyne-1-ol is prepared in a manner similar to the one used for the preceding compound, and the desired product is recovered with a quantitative yield.

Step 3: The product of the preceding step is transformed into β-julolidine cinnamaldehyde by heating it at 50° C. for 1 h in a mixture of acetic acid/water as in step 3 of the synthesis of compound (6).

Step 4: 0.68 g of 5,7-dimethoxy-3-methyl-1-naphthol are reacted with 0.85 g of Ti(OEt)$_4$ in 50 mL of toluene with reflux for 30 min, and then 0.94 g of the compound of the preceding step, which has first been dissolved in 25 mL of toluene, is added. The mixture is maintained with reflux for 2 h with azeotropic distillation of water through a Dean Stark condenser. The medium is then hydrolyzed with 40 mL of water, and the organic phase is recovered. Compound (9) is then purified by chromatography on a column of alumina using a mixture of diisopropyl ether/THF (85/15) as eluant followed by a crystallization in ethanol. 80 mg of a powder are obtained. The structure of the compound is confirmed by NMR spectroscopy.

Example 10

Incorporation of the compounds in a polyacrylate

General procedure: $10^{-4}$ mol of each one of the compounds are dissolved in 100 g of tetraethoxylated bisphenol A dimethacrylate (marketed under the name DIACRYL 121 by the company AKZO) also containing 40 mg of 2,2'-azobis (2-methylbutyronitrile). The solution is then degassed, rendered inert with argon, and then it is poured into a lens-shaped glass mold having a diameter of 8 cm and a thickness of 2 mm. The mold is then placed in an oven at 70° C. for 12 h. After removal from the mold, a transparent and rigid lens is obtained. Under solar irradiation, the glass rapidly develops a purple or intense blue coloration and it again becomes colorless in darkness. The photochromic characteristics are given in Table I below. After 15 min of exposure to a Xenon lamp, the UV-visible spectrum is recorded, and the λmax values of the two principal bands and their absorbances by Induced Optical Density (IOD) are measured. The absorbances are also measured after a 5-in discoloration in darkness.

Structures of compounds 1–9 according to the invention and of Comparative Example C1.

Compound (1)
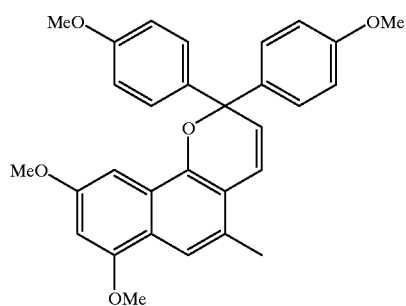
Compound (2)
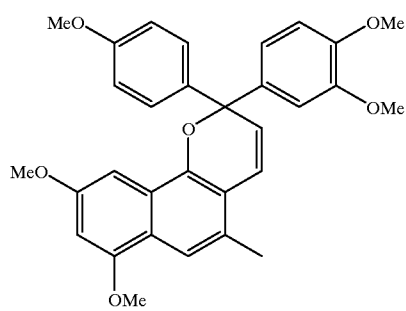
Compound (3)
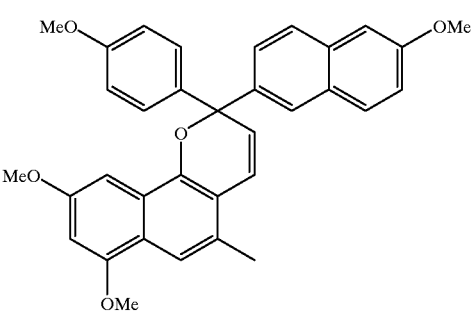
Compound (4)
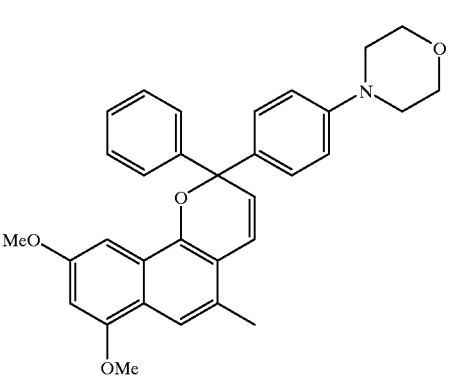
-continued
Compound (5)
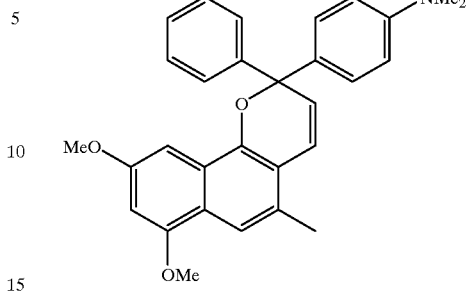
Compound (6)
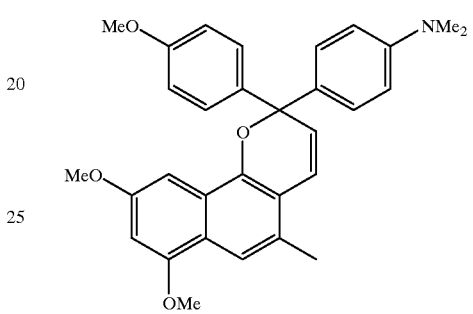
Compound (7)
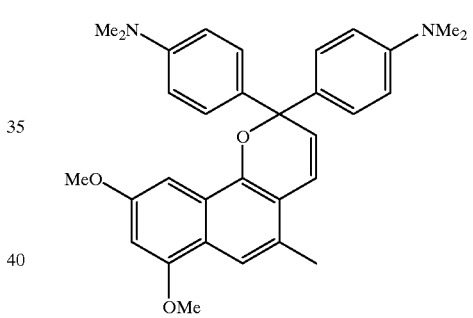
Compound (8)
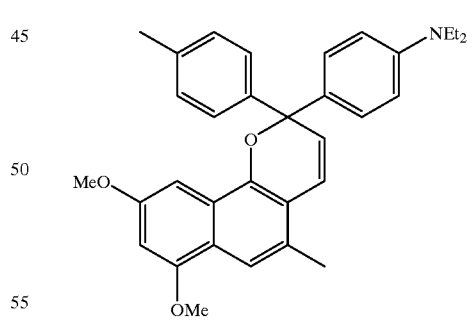

15
-continued

Compound (9)

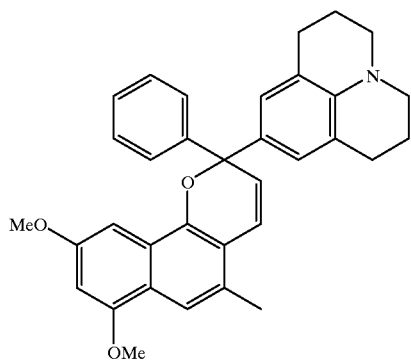

Compound C1

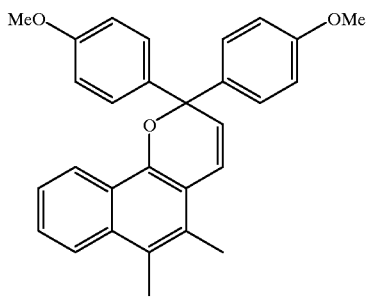

TABLE 1*

| Example | λ max band 1 (IOD after 15 min) | λ max band 2 (IOD after 15 min) | IOD band 2 after 5 min of discoloration |
|---|---|---|---|
| 1 | 440 (0.8) | 552 (0.7) | 0.4 |
| 2 | 444 (0.9) | 552 (0.8) | 0.6 |
| 3 | 444 (0.9) | 556 (0.8) | 0.7 |
| 4 | 470 (0.6) | 564 (0.7) | 0.5 |
| 5 | 492 (0.8) | 582 (1.3) | 0.7 |
| 6 | 488 (0.4) | 582 (0.7) | 0.4 |
| 7 | 476 (0.4) | 602 (0.6) | 0.4 |
| 8 | 496 (0.7) | 588 (1.1) | 0.6 |
| 9 | 518 (0.7) | 606 (1.2) | 0.8 |
| C1 | 422 (0.4) | 502 (0.6) | 0.4 |

*Described in Research Disclosure No. 36 144.

The results clearly demonstrate that the compounds of the invention have higher λmax values (550–610 nm for the second band and 440–518 nm for the second band), and most of them display much higher induced optical density compared to compound C1, having no methoxy groups on the naphthyl ring of the naphthopyran. In addition, it has been observed that the UV λmax of the compounds according to the invention have undergone a bathochromic shift of approximately 7 nm in comparison to compound C1 (382 nm versus 365 nm for compound C1). This shift consequently allows a better sensitivity to the UV radiation of the solar spectrum.

16

What is claimed is:
1. Compounds having the following general formula (I)

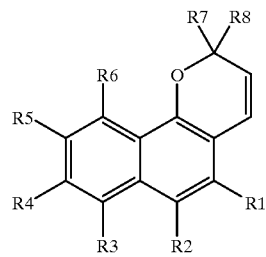

in which:
R1, R2, R4 and R6 are identical or different and they represent, independently
hydrogen,
a halogen,
a linear or branched alkyl group comprising 1–12 carbon atoms,
a cycloalkyl or bicycloalkyl group comprising 3 to 12 carbon atoms,
a linear or branched alkoxy group comprising 1–12 carbon atoms,
a linear or branched haloalkyl or haloalkoxy group comprising 1–6 carbon atoms,
a linear or branched alkenyl or alkynyl group comprising 1–12 carbon atoms,
a methacryloyl group or an acryloyl group,
an epoxy group having the formula

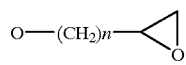

in which n=1, 2 or 3,
an aryl or aryloxyl group, whose aryl group comprises 6–24 carbon atoms, or a heteroaryl or heteroaryloxy group whose heteroaryl group comprises 4–24 carbon atoms and at least one heteroatom selected from the group consisting of sulfur, oxygen and nitrogen, the aryl or heteroaryl group optionally substituted by at least one substituent selected from:
a halogen,
a linear or branched alkyl group comprising 1–6 carbon atoms,
a linear or branched alkoxy group comprising 1–6 carbon atoms,
a linear or branched haloalkyl or haloalkoxy group comprising 1–6 carbon atoms,
an —NH$_2$ group,
an NHR group, where R represents a linear or branched alkyl group comprising 1–6 carbon atoms,
a NR'R" group, where R' and R", which may be identical or different, independently represent a linear or branched alkyl group comprising 1–6 carbon atoms or they represent, together with the nitrogen atom to which they are bound, a 5–7-member ring which can comprise at least one other heteroatom selected from the group of oxygen, sulfur and nitrogen, said nitrogen being optionally substituted by a linear or branched alkyl group comprising 1–6 carbon atoms,
an aralkyl or heteroalkyl group whose linear or branched alkyl group comprises 1–4 carbon atoms and whose aryl and heteroaryl groups are as defined above, an —NH$_2$, —NHR, NR'R", CONH$_2$, CONHR or CONR'R" group, where R, R' and R" are as defined above, an OCOR' or COOR' group, where R' represents a linear or branched alkyl group comprising 1–6 carbon atoms or a cycloalkyl or bicycloalkyl group comprising 3–12 carbon atoms or an aryl or heteroaryl group as defined above, a polyether, polyamide, polycarbonate, polycarbamate, polyurea or polyester residue;

R7 and R8 are identical or different and they represent independently:

a linear or branched alkyl group comprising 1–12 carbon atoms, a cycloalkyl group comprising 3–12 carbon atoms, an aryl or heteroaryl group as defined above for R1, R2, R4 and R6, the julolidin-9-yl group, or the two groups R7 and R8 together form an adamantyl, norbornyl, fluorenylidene or di(C1–C6 alkyl) anthracenylidene or spiro(C5–C6 cycloalkyl) anthracenylidene group; characterized in that R3 and R5 are identical or different and they each represent a linear or branched alkoxy group comprising 1–6 carbon atoms.

2. Compounds according to claim 1, characterized in that R3 and R5 are methoxy groups.

3. Compounds according to claim 1, characterized in that R1, R2, R4 and R6 are hydrogen atoms or linear or branched alkyl groups comprising 1–6 carbon atoms.

4. Compounds according to claim 1, characterized in that they have the following structures (I1) and (I2)

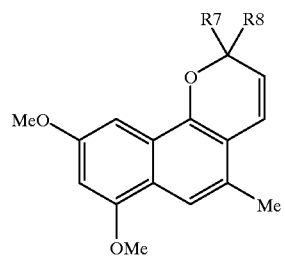

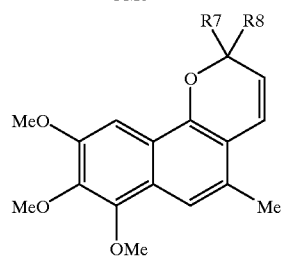

in which R7 and R8 are as defined in claim 1.

5. Compounds according to claim 1, characterized in that R7 and R8 are aryl or heteroaryl groups selected from the group consisting of phenyl, naphthyl, biphenyl, pyridyl, furyl, benzofuryl, dibenzofuryl, N(C1–C6 alkyl)carbazole, thienyl, benzothienyl or dibenzothienyl groups, optionally substituted by at least one C1–C5 alkoxy, C1–C5 alkyl, C2–C12 amine, C6–C12 aryl, or CF$_3$ group.

6. Compound according to claim 1, characterized in that R1, R2, R4 and R6 are identical or different and they represent, independently hydrogen, fluorine, chlorine or bromine, a linear or branched alkyl group comprising 1–12 carbon atoms, a cycloalkyl or bicycloalkyl group comprising 3 to 12 carbon atoms, a linear or branched alkoxy group comprising 1–12 carbon atoms, a linear or branched fluoroalkyl group comprising 1–6 carbon atoms, a vinyl or allyl group, a methacryloyl group or an acryloyl group, an epoxy group having the formula

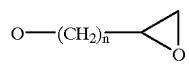

in which n=1, 2 or 3, an aryl or aryloxyl group, whose aryl group comprises 6–24 carbon atoms, or a heteroaryl or heteroaryloxyl group whose heteroaryl group comprises 4–24 carbon atoms and at least one heteroatom selected from the group consisting of sulfur, oxygen and nitrogen, the aryl or heteroaryl group being optionally substituted by at least one substituent selected from:

fluorine, chlorine or bromine, a linear or branched alkyl group comprising 1–6 carbon atoms, a linear or branched alkoxy group comprising 1–6 carbon atoms, a linear or branched fluoroalkyl group comprising 1–6 carbon atoms, an —NH$_2$ group, a NHR group, where R represents a linear or branched alkyl group comprising 1–6 carbon atoms, a NR'R" group, where R' and R", which may be identical or different, independently represent a linear or branched alkyl group comprising 1–6 carbon atoms or they represent together with the nitrogen atom to which they are bound a 5–7-member ring that comprise at least one other heteroatom selected from the group of oxygen, sulfur and nitrogen, said nitrogen being optionally substituted by a linear or branched alkyl group comprising 1–6 carbon atoms, an aralkyl or heteroalkyl group whose linear or branched alkyl group comprises 1–4 carbon atoms and whose aryl and heteroaryl groups are as defined above, a —NH$_2$, —NHR, NR'R", CONH$_2$, CONHR or CONR'R" group, where R, R' and R" are as defined above, an OCOR' or COOR' group, where R' represents a linear or branched alkyl group comprising 1–6 carbon atoms or a cycloalkyl or bicycloalkyl group comprising 3–12 carbon atoms or an aryl or heteroaryl group as defined above, a polyether, polyamide, polycarbonate, polycarbamate, polyurea or polyester residue.

7. Compounds according to claim 1, characterized in that they have photochromic properties.

8. Compounds according to any one of claim 7, characterized in that the groups R1, R2, R4, R6, R7 and R8 of formulas (I), (I1) and (I2) according to the invention comprise and/or form at least one polymerizable and/or crosslinkable reactive group, selected from the following:

alkenyl, methacryloyl, acryloyl, acryloxyalkyl, methacryloxyalkyl and epoxy.

9. (Co)polymer and/or crosslinked compound obtained by polymerization and/or crosslinking of at least one monomer consisting of at least one compound according to claim 8.

10. Photochromic composition, characterized in that it comprises:

at least one compound according to claim 7 and/or at least one (co)polymer according to claim 8, and, optionally, at least one other photochromic compound and/or at least one dye and/or at least one stabilizer.

11. (Co)polymer matrix, characterized in that it comprises at least one compound according to any one of claims 1–9.

12. (Co)polymer matrix, characterized in that it comprises at least one compound according to claim 10.

13. Matrix according to claim 11, characterized in that the (co)polymer is selected from the following:

alkyl, cycloalkyl, aryl or arylalkyl poly(mono-, di-, tri-, tetra)acrylate or poly(mono-, di-, tri-, tetra) methacrylate, optionally halogenated or comprising at least ether and/or ester and/or carbonate and/or carbamate and/or thiocarbamate and/or urea and/or amide group; polystyrene, polycarbonate (e.g., bisphenol A polycarbonate, poly(carbonate of diallyl diethylene glycol), polyepoxy, polyurethane, polythiourethane, polysiloxane, polyacrylonitrile, polyamide, aliphatic or aromatic polyester, vinyl polymers, cellulose acetate, cellulose triacetate, cellusose acetate-propionate or polyvinylbutyral, copolymers of two or more types of monomer or mixtures of the above-mentioned polymers.

14. Ophthalmic or sun-protection article comprising at least one compound according to claims 1–8.

15. Ophthalmic or sun-protection article comprising at least one copolymer according to claim 9.

16. Ophthalmic or sun-protection article comprising at least one photochromic composition according to claim 10.

17. Article according to claim 14, characterized in that it consists of a lens.

18. Paneling and/or optical device comprising at least one compound according to claims 1–8.

19. Paneling and/or optical device comprising at least one (co)polymer according to claim 9.

20. Paneling and/or optical device comprising at least one photochromic composition according to claim 10.

21. Paneling and/or optical device comprising at least one matrix according to claim 11 or 12.

* * * * *